United States Patent [19]

Rayman et al.

[11] Patent Number: 4,966,588
[45] Date of Patent: Oct. 30, 1990

[54] DEVICE SUITABLE FOR THE ADMINISTRATION OF A THERAPEUTIC SUBSTANCE

[75] Inventors: Gerrard A. Rayman, Martlesham Heath, Nr. Ipswich; Harvey L. Sugarman, Colchester; Ivan P. Harris, Clacton-on-Sea, all of England

[73] Assignee: H. G. Wallace Limited, Essex, England

[21] Appl. No.: 170,383

[22] PCT Filed: Jul. 24, 1987

[86] PCT No.: PCT/GB87/00527
§ 371 Date: May 23, 1988
§ 102(e) Date: May 23, 1988

[87] PCT Pub. No.: WO88/00842
PCT Pub. Date: Feb. 11, 1988

[30] Foreign Application Priority Data
Jul. 25, 1986 [GB] United Kingdom ............... 8618253

[51] Int. Cl.$^5$ ............................................. A61M 5/00
[52] U.S. Cl. .................... 604/165; 604/167; 604/283
[58] Field of Search ............. 604/164, 165, 167, 256, 604/244, 283

[56] References Cited

U.S. PATENT DOCUMENTS

| 3,097,646 | 7/1963 | Scislowicz ........................ 604/167 |
| 4,059,105 | 11/1977 | Cutruzzula . |
| 4,121,585 | 10/1978 | Becker . |
| 4,194,504 | 3/1980 | Harms . |
| 4,559,043 | 12/1985 | Whitehouse et al. ........... 604/283 X |

FOREIGN PATENT DOCUMENTS

| 4169704 | 1/1986 | European Pat. Off. . |
| 2139004 | 2/1973 | Fed. Rep. of Germany ...... 604/167 |
| 3147609 | 6/1983 | Fed. Rep. of Germany . |
| 2474317 | 7/1981 | France . |

Primary Examiner—Stephen C. Pellegrino
Attorney, Agent, or Firm—Cushman, Darby & Cushman

[57] ABSTRACT

The invention relates to a device suitable for use in the intermittent or even continuous administration of a therapeutic substance such as insulin or morphine.

The device comprises a cannula of biocompatible plastics material for indwelling in a patient and defining a through-passage, together with a hub also defining a through-passage. The respective cannula and hub passages are isolatable from each other by separator means such as a self-sealing diaphragm disposed between them. In the device the arrangement of the respective passages themselves together with said diaphragm or the like is such as to permit a needle to penetrate the hub and cannula through them and, when necessary, to extend beyond the distal end of the cannula. The through-passage of the hub is also constructed and arranged so that it guides an injection needle passed therethrough to pass through the diaphragm at a position where the needle is aligned with the through-passage of the cannula.

The device enables sixteen or more injections to be made without trauma and at a single site.

22 Claims, 3 Drawing Sheets

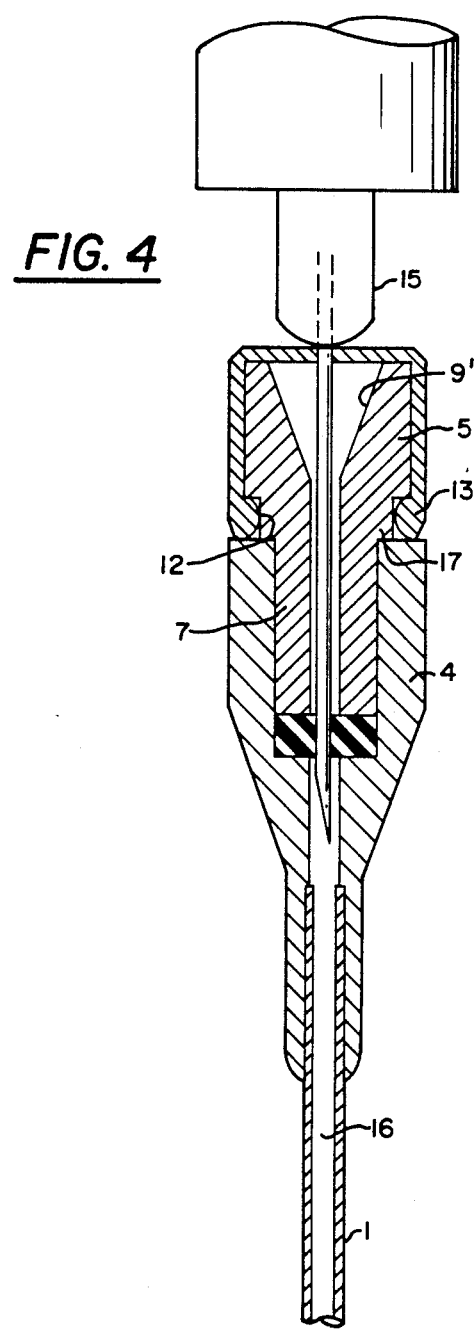

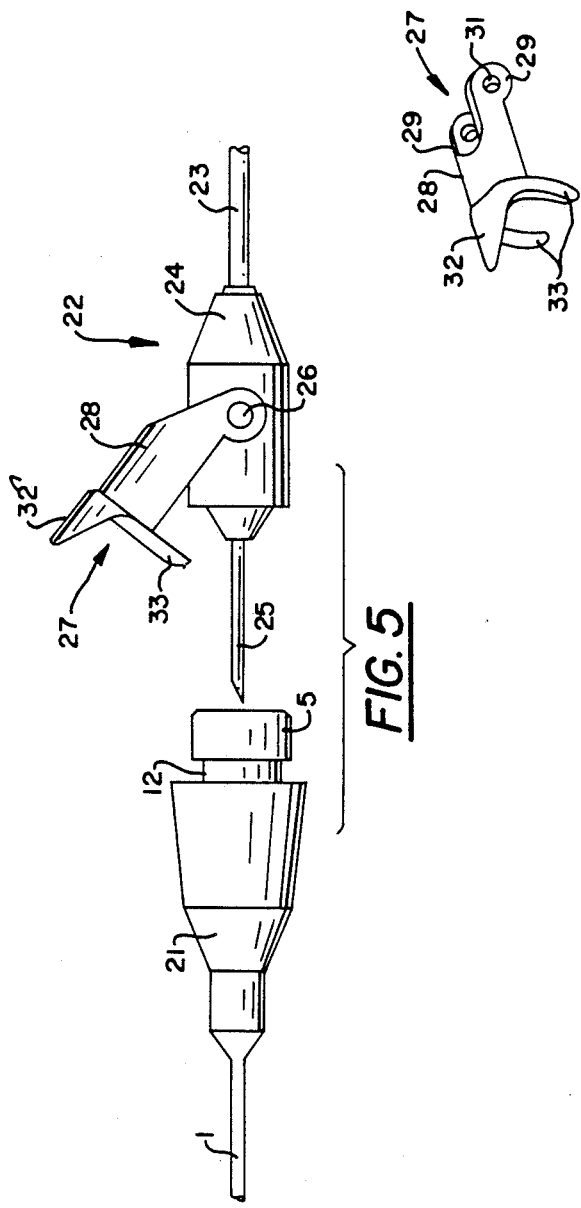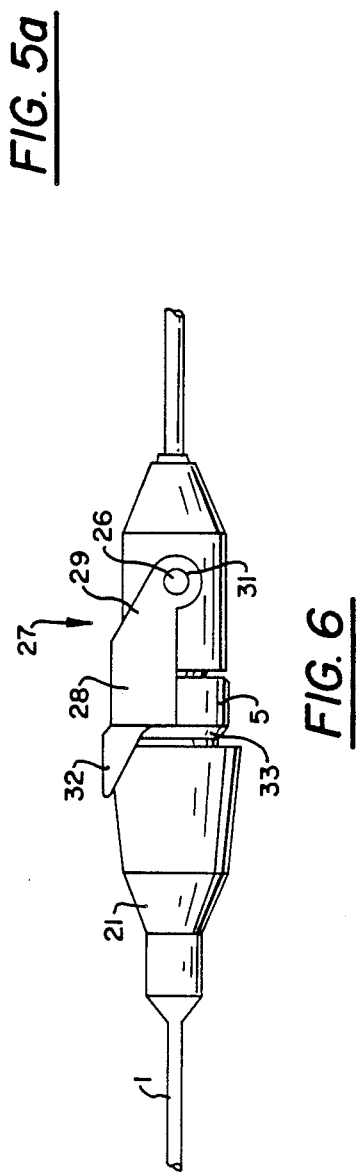

DEVICE SUITABLE FOR THE ADMINISTRATION OF A THERAPEUTIC SUBSTANCE

The present invention relates to a device suitable for the administration of a therapeutic substance, for example insulin, especially but not necessarily on an intermittent basis.

Insulin-dependent diabetics rely upon subcutaneous doses of insulin administered, and usually self-administered, by means of a syringe and a hypodermic needle. This involves the psychological trauma of self-injection, as well as the inconvenience of the overall procedure. Insulin may also be delivered by electrical, mechanical or hand-operated pumps.

Alternatively, it is also possible to use an indwelling needle through which insulin may be administered. The facility to give injections via indwelling needles is not new (see, for example U.S. Pat. No. 4,568,335), but there are two problems with such indwelling needles as currently available. First, the needles are sharp and made of rigid steel, which can be painful in situ; and secondly, in the injection port attached to the needle there is a large "dead-space", that is the space in the device within which insulin will be withheld instead of being expressed to the patient, which gives rise to problems not merely the problems involved in taking account of the dead-space when calculating doses of insulin, but also the further problems which arise when injecting more than one species of insulin. Furthermore, the kind of needles employed for this purpose and their associated apparatus are often designed for giving large volumes of solution, or for sampling blood. Still further, as shown for example in the above-mentioned United States Patent Specification the connection between the feed syringe or the like and the needle cannot be broken, since there is no seal in or associated with the needle itself.

In an effort to eliminate dead-space problems, there has been marketed in the U.K. a so-called "button" infuser, which is said to have a nominal "dead-space" volume of less than 0.33 units of U-100 insulin. However, that "button" infuser again has a steel needle, leading to discomfort; and, while this device is self sealing, it is difficult to ensure that the intermittent injection needle (which has to be inserted into the indwelling needle) is always during its insertion accurately placed, so that first it does not over-penetrate and engage the plastics material in the hub of the indwelling needle, and so that secondly it does not under-penetrate and fail to enter the indwelling needle lumen beyond the self-sealing diaphragm. The cause of this difficulty is that in this known "button" infuser the self-sealing diaphragm takes the form of a relatively thick seal at the mouth of the device; or in other words, the seal is positioned so that it must be pierced before the device can be entered, and this in practice causes entry problems. Thus, for example, where the device is worn say on the patient's abdomen, the patient must look down and, with a fairly restricted view of the mouth of the device, attempt to penetrate a relatively thick seal, without either under-penetrating or over-penetrating as described above.

We have now found surprisingly that the disadvantages of the known "button" infuser can be avoided, while at the same time still having a dead space of only relatively small volume, by disposing the seal in the body of a cannula hub, the seal being disposed not only adjacent the hub-end connected to the cannula, but also at the distal end of a needle guide passage through the hub, which ensures correct alignment of the injection needle as it passes through the hub and penetrates the seal.

Accordingly, the present invention provides a device suitable for use in the intermittent or even continuous administration of a therapeutic substance (such as insulin), which device comprises a cannula of biocompatible plastics material for indwelling in a patient and defining a through-passage (lumen), together with a hub also defining a through-passage, the respective cannula and hub passages being isolatable from each other by separator means (such as a self-sealing diaphragm) disposed between them, the arrangement of the respective passages themselves and together with said separator means being such as to permit a needle to penetrate the hub and cannula through them and, when necessary, to extend beyond the distal end of the cannula, the through-passage of the hub also being so constructed and arranged as to guide an injection needle passed therethrough so that the needle thus guided will pass through the separator means at a position where the needle is aligned with the through passage of the cannula.

In use the device of the invention can be positioned with its cannula implanted subcutaneously in the patient by means of a skin-puncture needle which may be already disposed in the device or inserted therein when required, and which extends beyond the distal end of the cannula Once the cannula of the device has thus been implanted, the skin-puncture needle is withdrawn, and the device can be taped in place to be left in situ for use in the administration of one or more doses of insulin or the like as necessary. For example, but fairly typically, the device may be left in situ for four days, and over that period of time up to 16 doses or more of insulin may be injected through the device, effectively involving only the single initial skin puncture.

For the purpose of giving an injection of insulin or the like the needle of a hypodermic syringe containing the insulin or the like is passed along the through-passage in the hub. Once it reaches the end of that passage, the needle passes through the separator means. Preferably, its movement past a position where its tip is just beyond the separator means is then prevented by including in the device of the invention over penetration-restraining means. Conveniently, this can be accomplished by arranging the hub so that the overall penetrable length of the through-passage therein is just a little shorter than a standard hypodermic needle. For example, one typical standard hypodermic needle for insulin injection is an 11 mm needle.

In the device of the invention, the through passage in the cannula and the through-passage in the hub are separated by separator means. While in theory any suitable separator means could be employed, for example mechanical separator means such as a valve, it is in practice generally preferred to employ a self sealing diaphragm. Such a diaphragm may comprise a variety of self-sealing elastomeric materials, for example, natural rubber, silicone rubber or a suitable grade of any other elastomeric polymer.

By providing a hub having a through-passage and which includes a self-sealing diaphragm or like separator means at the distal end of the passage adjacent the entrance to the cannula, accurate placement of the injection needle can be accomplished. Thus, in the first place accurate alignment between the needle and the cannula lumen can be accomplished by the arrangement of the through-passage in the hub; and secondly, the length of the hub can be chosen so that the desired amount of penetration of the diaphragm or the like is achieved, but no more.

In the device of the invention, the nominal "deadspace" volume generally may be any chosen volume of about 0.75 units of U-100 insulin or below. Thus, while in theory larger "dead-space" volumes may be chosen—since notionally at least the self-sealing diaphragm or the like always holds a small volume of insulin in the cannula passage beyond the diaphragm seal—nevertheless because "dead-space" volumes of about 0.75 units of U-100 insulin or below are easily achieved with the device of the invention, as described herein, and because the smaller the "dead-space" volume the more flexible the device can be in terms of the ability to avoid the need to flush when changing insulin dosage or species, "deadspace" volumes below the figure stated above are generally preferred. More preferably, however, the "dead-space" volume should be in the range of from about 0.5 to about 0.3 units of U-100 insulin.

Furthermore, in the device of the invention the mouth of the through-passage in the hub most remote from the cannula is desirably so shaped that the passage has a conical or funnelled entrance zone. By providing a conical or funnelled entrance zone, penetration of the mouth of the through-passage in the hub by the hypodermic needle is facilitated even when the cannula is positioned in situ, and even though the patient's view of the mouth of the through-passage may be restricted. Also, the conical or funnelled entrance zone provides a guide portion permitting easy penetration of the mouth of the through-passage even where the passage mouth is covered, as is preferred, by a self-sealing cap or the like, as described below. It will be appreciated that ingress of dirt or other undesirable material into the device can be avoided if the hub includes means such as a cap to prevent such ingress.

As indicated above, the device of the invention generally may remain in situ for a period in the region of about 4 days, with a typical period being say from about 2 to about 5 days. Since the device includes a cannula of biocompatible plastics material, irritation generally is kept to a minimum, and the plastics cannula is thus less noticeable to the wearer once placed in situ than a corresponding steel cannula. Moreover, the patient can feel confident once the device is in situ that the next-following series of injections (say 16 or more further injections) can be accomplished without trauma and, furthermore, that no insulin loss will occur. That is because the injection needle is securely guided to proper placement in the injection port, and generally cannot be misdirected or misplaced.

Preferably, the cannula comprises a flexible synthetic plastics material, generally formed of one or more synthetic polymers, for example, of one or more fluorocarbons such as "Teflon". It is of course especially preferred that the cannula should comprise a medical-implant grade synthetic polymer. In addition, it is also preferred that the hub should comprise a biocompatible material suitable for use with drugs and next to skin. Examples of such materials are polypropylene and polyurethane materials.

Furthermore, in the device of the invention the hub is preferably a two-part hub-assembly, preferably with the separator means located between the two parts of the hub. More preferably, in such a construction a first hub-component comprises a body defining an axial bore which at its distal end is adapted to receive the proximal end of the cannula, whereby the through-passage of the cannula is positioned in communication with the bore, and at its other end a socket communicating with the bore and adapted to receive (mate with) a plug portion of a second hub-component, also comprising a body defining an axial bore, the bores in the respective first and second hub-components being aligned to communicate with each other and together defining the through-passage in the hub assembly By providing such a two-part construction, a self-sealing diaphragm can then be sandwiched between the two hub-components e.g. between the distal end of the plug-portion and the base of the socket.

Preferably, the first hub-component includes an elongated nose portion at its distal end, within which a significant portion of the proximal end of the cannula can be accommodated, thereby providing support for the cannula and a means of securing the cannula to the hub, for example, by adhering the outside of the cannula to the inside of the nose. Additionally or alternatively, the bore in the first hub-component may be of greater diameter than the diameter of the through-passage, where it accommodates the tip of the proximal end of the cannula, thus providing an annular abutment for the tip of the proximal end of the cannula, to permit securing of the cannula to the hub.

In order to minimize pain during the initial injection through the patient's skin, the cannula can advantageously be shaped at its distal tip so that it tapers towards and close to the projecting tip of a skin-puncture needle (when the latter is disposed within the device, to enable it to penetrate the skin), and so that its front edges are relatively smooth.

Also, while we have indicated above that the device may be taped in place, other fixing means may be employed. Thus, for example, the hub of the device may include a self-adhesive support portion to enable the hub to adhere to the patient's skin when pressed thereagainst.

The device of this invention has been described above mainly in relation to its use with insulin, but it is to be understood that its utility is not necessarily confined to the administration of insulin but extends to the administration of any therapeutic substance which requires the patient to be injected (or above all to inject himself) frequently—say a number of times in each day. Thus, for instance, the device can prove valuable in the regular administration of morphine.

Furthermore, while the device has been primarily designed and therefore is particularly suitable for self-administration on an intermittent basis, it should be appreciated that it may also be used in conjunction with apparatus for continuous administration. Thus, besides being useful in the case where injections are given through the cannula as and when required (either by means of a standard syringe or a cartridge device) the hub may be adapted to be connected to means continuously to supply a therapeutic substance such as insulin or morphine. Such means are currently available and comprise a reservoir, a pump, a supply line and a needle for injection purposes. Also, various kinds of sophisticated electronic means may be included to achieve any necessary or desired control over the doses pumped from the reservoir to the needle via the supply line.

For such use, the device preferably will include a hub having means to provide or accommodate a supply line lock fitment. Thus, for example, the hub may be formed with say one or more Luer lock lugs, or with means to accommodate say a Luer lock adaptor.

Alternatively and preferably, the hub is of a two part hub-assembly as described previously, and the hub components are arranged so that the plug-portion of the second hub-component includes an annular flange, and the plug-portion mates with the socket in the first hub-component in such a manner that an annular locking groove is formed between the flange and the end of the first hub-component adjacent the flange Such an annular groove may be used to accommodate the front arms of a clip, for example, a hinged clip like that described in co-pending British Patent Application No. 85-17976 (Publication No. 2,161,709A) and European Patent Application No. 85-30-5093.8 (Publication No. EP 0169704A). A said clip may be defined as one having a body portion including at or adjacent one end means, such as a pair of opposed depending arms, engageable with the supply line or supply line connector, and at or adjacent its other end a pair of opposed depending arms engageable with the groove, the said means being arranged to permit the said arms engageable with the groove to move into and out of engagement.

Preferably such a clip may be one for use with a supply line which includes a pair of trunnion pins upstanding on either side of an end portion of the line. The clip then may be formed with a first pair of opposed arms each including an aperture so that they can be sprung over the trunnion pins and the clip thereby pivotably mounted on the end portion of the line.

The invention also includes a device as defined and described herein in combination with a skin puncture needle. Such a combination may be put up for use packaged together with the needle disposed in the device in a sterile pack. The pack preferably will include a self-sealing cap as described herein to prevent ingress of dirt in use.

In addition, the invention includes a device as defined and described herein in combination with a supply line arrangement. Preferably, in such a combination the supply line arrangement includes mounted on an end portion of the line a needle adapted to penetrate the separator means of the device and a pivotal clip engageable with the hub of the device to lock together the device and the supply line. More preferably, the hub may be a two-part hub-assembly as described above with an annular locking groove and the clip may be as defined above. Also, the supply line arrangement may include a reservoir and/or a pump and/or electronic control means as described above.

In order that the invention may be well understood a preferred embodiment thereof will now be described in more detail, though only by way of illustration, with reference to the accompanying drawings, in which:

FIG. 4 is a mainly cross-sectional view of the same embodiment of the device, generally similar to FIG. 2 but on an enlarged scale, and in which the skin-penetration needle has been removed and replaced by the hypodermic injection needle of a syringe;

FIG. 5 is a diagrammatic side view of a combination of a device in accordance with the invention shown in unlocked association with a supply line arrangement;

FIG. 5(a) shows the clip of FIG. 5 separate from the supply line arrangement; and FIG. 6 shows the combination of FIG. 5 locked together.

Figure 1:
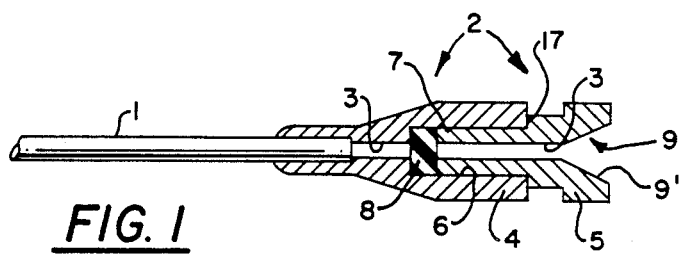
FIG. 1 is a mainly cross-sectional view, taken in a plane through the axis, of an embodiment of the device of the invention.

Referring to FIGS. 1 to 4 of the drawings, the device shown comprises a cannula 1 having a delivery (through) passage or lumen 16. The cannula is formed of biocompatible flexible synthetic plastics material and, therefore, is capable of indwelling in a patient for a period of several days after subcutaneous insertion thereof. The proximal end of the cannula 1 is mounted and secured (e.g. by adhesive) at the distal end of a two-part hub assembly, generally indicated by the numeral 2, also formed of a biocompatible but relatively rigid plastics material, and having a through-passage 3 passing axially therethrough which communicates with the delivery passage or lumen 16 within the cannula 1. The hub-assembly 2 comprises a first hub-component 4 and a second hub-component 5, each having an axially-disposed bore therein which, in the assembled position (as shown), is aligned with the axially-disposed bore in the other hub-component, and which together constitute the through-passage 3. The hub assembly 2 is formed by mating a cylindrical socket 6 in the proximal end of the first hub-component 4 with a plug-portion 7 on the distal end of the second hub-component 5. An annular collar 17 around hub-component 5 prevents the plug portion 7 from mating fully with the socket 6 in the first hub-component 4 and, within the cylindrical chamber between the base of the socket 6 and the end of the plug-portion 7, there is accommodated a self-sealing diaphragm 8, formed of silicone rubber or another elastomeric polymer. The diaphragm 8 is thus sandwiched between the hub-components 4 and 5, blocking communication between the axial bores therein and thus normally sealing the through-passage 3. However, the diaphragm 8 may easily be penetrated by a needle which is passed down the through-passage 3 to penetrate through the diaphragm.

In order to implant the indwelling cannula 1 subcutaneously in a patient, in the manner which will be described in more detail hereinafter, a skin-penetration needle 14 (see FIGS. 2 and 3) is passed through the device down through-passage 3 until its tip protrudes beyond the distal end of cannula 1. It will be seen that, in order to ease the implantation of the cannula 1 subcutaneously into the patient, its distal end 1' is externally tapered and fitted as closely as possible about the protruding end of the skin-penetration needle 14.

The proximal end of the second hub-component 5 is provided with an open-mouthed, conical indent generally designated by the numeral 9, whose conical walls 9' are co-axial with and whose apex communicates with the through-passage 3. As can best be appreciated from FIGS. 2 and 4, a skin-penetration needle (FIG. 2) or a hypodermic injection needle (FIG. 4) entering the device, is funnelled into alignment with the through passage 3 by this open-mouthed conical indent 9.

Figure 2:
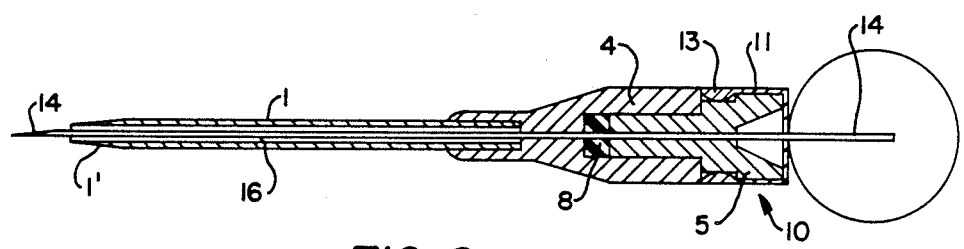
FIG. 2 is an essentially similar, mainly cross sectional view, of the embodiment of FIG. 1, again taken in a plane through the axis of the device, showing a cap-like closure member mounted thereon to prevent ingress of dirt, and a skin-penetration needle fitted therethrough in its operative, skin-penetrating position.
Figure 3:
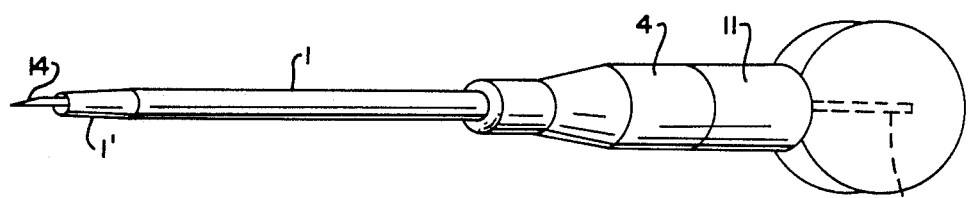
FIG. 3 is a non-sectional external view of the embodiment of FIG. 2, taken in slight perspective from the distal end of the skin-penetration needle.

As appears from FIGS. 2 and 4, in order to prevent ingress of dirt or other undesirable material into the open mouth of the conical indent 9 defined by walls 9', a tubular-skirted cap generally indicated by the numeral 10, and formed of elastomeric material, is removably fitted across the otherwise open mouth of the conical indent 9. There it is held in position by its depending tubular walls 11 adapted to embrace part of the cylindrical outer surface of the main body portion of the second hub-component 5.

As best appears from FIG. 4, in order the better to retain the cap 10 in place and to ensure dirt-proof engagement between the tubular walls 11 of the cap 10 and the outer surface of the main body-portion of the second hub-component 5, the distal end of the latter, adjacent the plug portion 7, is provided with an annular groove 12, within which there is accommodated a bulbous sealing ring 13 formed around the skirt-edges of the tubular walls 11 of the cap 10.

In use, a skin-penetration needle 14 (see FIGS. 2 and 3) is passed through the cap 10, funnelled by the conical indent 9 into the through-passage 3 and, after piercing the self-sealing diaphragm 8, enters and passes through the lumen 16 of the cannula 1, until it extends somewhat beyond the tapered distal end 1' thereof. With the skin-penetration needle thus located, the cannula 1 the device is then subcutaneously implanted in the patient, the hub-assembly 2 is taped or otherwise secured in place upon the patient (e.g. his abdomen) and the skin-penetration needle is withdrawn, leaving the device indwelling in the patient. There it may remain for several days ready for intermittent or continuous use, as required, for the administration (especially the self-administration) of insulin, morphine or any other therapeutic substance.

Whenever it is appropriate to administer such a therapeutic substance, the needle of the hypodermic injection syringe containing the substance is, as shown in FIG. 4, passed in a similar manner through the cap 10. Again the needle is funnelled by conical indent 9 into the through-passage 3, and then pierces the self sealing diaphragm 8, but this time is there arrested when the syringe-body 15 abuts against the cap 10. Thus, the hypodermic injection syringe is placed in an ideal location adjacent the end of the cannula 1 for the discharge of therapeutic substance from the syringe to the patient through the device.

Referring to FIGS. 5, 5(a) and 6, the combination there shown comprises a device 21 in accordance with the invention, for example, as described above, and a supply line arrangement generally designated by the numeral 22. The supply line arrangement includes a supply line 23 e.g. a fine bore line, through which a therapeutic substance such as insulin or morphine may be fed e.g. by a pump arrangement, and an end portion 24. The end portion 24 includes a needle 25 e.g. corresponding to the needle of the syringe shown in FIG. 4, and a pair of trunnion pins 26 (only one shown).

Mounted on the end portion 24 via the trunnion pins 26 is a locking clip generally designated by the numeral 27. The locking clip 27 comprises a body portion 28 having a first pair of opposed depending arms 29 engageable with the trunnion pins 26 via through apertures 31 whereby the clip 27 can be pivotably mounted on the end portion 24 as shown. The body portion 28 also has a nose portion 32 and a second pair of opposed depending arms 33 which are engageable with annular groove 12 (see also FIG. 4) when the needle 25 is passed into the device 21 so that a configuration of needle and device the same as or similar to that shown in FIG. 4 is achieved.

Thus, the supply line arrangement 22 and the device 21 may be locked together as shown in FIG. 6 so that the patient may receive a therapeutic substance through the line 23. Thereafter, when treatment is complete the combination may be unlocked by inserting a finger under nose portion 32 and lifting the arms 33 out of engagement with the annular groove 12, thus releasing the device 21 from the supply line arrangement 22.

In the accompanying drawings to which the above description relates the relative sizes of certain parts of the device are altered or exaggerated for the purpose of clarity. However, it is to be understood that in practice say the cannula end 1', the lumen 16 and the passage 3 will be closely matched to the needle 14 e.g. as shown for the needle 14 and passage 3 in FIG. 2.

As will be appreciated from the above description, the invention provides a device in which accurate placement of the injecting or like needle can be accomplished both in terms of alignment and in terms of penetration. In particular, accurate placement in terms of alignment is achieved by providing in accordance with the preferred embodiments described above a hub defining a through-passage so constructed and arranged that the needle is constrained by the diameter of at least part of the through-passage and its alignment with the cannula lumen so that it must enter the lumen as it passes through the self-sealing diaphragm or other separator means rather than penetrate the cannula wall or otherwise be misaligned. Thus, the respective cannula and hub through-passages being at least essentially the same in diameter and at least essentially axially aligned lead to the desired accurate placement.

While the invention is illustrated above by way of example with reference to specific embodiments it is to be understood that the invention is not limited to what is described. Thus, for example, the body of clip 27 may be longer and arms 33 may engage the device 21 nearer its distal end e.g. in another annular groove formed therein beyond groove 12. In that manner the cap 10 may be left in situ in the combination of FIGS. 5 to 6. Furthermore, as will be appreciated, other arrangements may be employed and numerous variations may be made within the spirit of the invention defined by the scope of the claims which follow.

We claim:

1. A device suitable for use in the intermittent or even continuous administration of a therapeutic substance such as insulin, which device comprises:

a cannula of biocompatible plastics material for indwelling in a patient and defining a cannula through-passage;

a hub defining a hub through-passage; and a separator means, the respective cannula and hub through-passages being isolatable from each other by said separator means, said separator means being disposed between the proximal end of the cannula and the proximal end of the hub and the hub being operatively connected with the cannula, the respective said through-passages and said separator means serving, in use, to permit a needle to penetrate the hub and cannula through them and, when necessary, to extend beyond the distal end of the cannula, the through-passage of the hub also serving, in use, to guide an injection needle passed therethrough so that the needle thus guided will pass through the separator means at a position where the needle is aligned with the through-passage of the cannula;

said hub being a two-component hub assembly comprising a first hub component and a second hub component, and the separator means being located between the two components of the hub;

said first hub-component comprising a body defining an axial bore which at its distal end is adapted to receive the proximal end of the cannula, whereby the through-passage of the cannula is positioned in communication with the bore, and at its other end a socket communicating with the bore and adapted to receive a plug-portion of said second hub-component also comprising a body defining an axial bore, the bores in the respective first and second hub-components being aligned to communicate with each other and together defining said hub through-passage in the hub-assembly.

2. A device according to claim 1, including overpenetration-restraining means for preventing the tip of a hypodermic syringe injection needle from passing much beyond the separator means.

3. A device according to claim 2, wherein the overpenetration-restraining means are provided by arranging that the overall penetrable length of the through-passage in the hub is slightly shorter than a standard hypodermic needle to be used in conjunction with the device.

4. A device according to claim 1, having a dead-space volume of about 0.75 units of U-100 insulin or below.

5. A device according to claim 4, wherein said dead-space volume is from about 0.5 to about 0.3 units of U-100 insulin.

6. A device according to claim 1 wherein the mouth of the through-passage in the hub most remote from the cannula is shaped such that the passage has a conical or funnelled entrance zone.

7. A device according to claim 1 which includes a penetrable cap disposed at the proximal end of the hub, covering the entrance of the hub through-passage to prevent ingress of dirt or other undesirable material when an injection needle is not inserted therein.

8. A device according to claim 1 wherein the cannula comprises a flexible synthetic plastics material.

9. A device according to claim 8, wherein the cannula comprises medical-implant grade synthetic polymer.

10. A device according to claim 8 wherein the hub also comprises a biocompatable material suitable for use with drugs and next to skin.

11. A device according to claim 1, wherein the separator means is a self-sealing diaphragm sandwiched between the two hub-components.

12. A device according to claim 11, wherein the self-sealing diaphragm comprises a natural rubber, a silicone rubber or another self-sealing elastomeric polymer.

13. A device according to claim 1, wherein the first hub-component body includes an elongated nose portion at it distal end within which a portion of the proximal end of the cannula can be accommodated.

14. A device according to claim 13, wherein the bore in the first hub component is of greater diameter than the diameter of the through-passage where it accommodates the tip of the proximal end of the cannula, thus providing an annular abutment for the tip of the proximal end of the cannula to permit securing of the cannula to the hub.

15. A device according to claim 1, wherein the cannula is shaped at its distal tip so that the cannula tapers towards and close to the projecting tip of a puncture needle, when the latter is disposed within the device, to enable the device to penetrate the skin, and so that front edges thereof are relatively smooth.

16. A device according to claim 1, which includes a self-adhesive support portion on the hub to enable the hub to adhere to the patient's skin when pressed thereagainst.

17. A device according to claim 1 which includes a hub having means to accommodate a supply line lock fitment.

18. A device according to claim 17, wherein the hub is formed with one or more Luer lock lugs or with means to accommodate a Luer lock adaptor.

19. A device according to claim 1, wherein the first and attend hub-components are arranged so that the plug-portion of the second hub-component includes an annular flange, and the plug-portion mates with the socket in the first hub-component in such a manner that an annular locking groove is formed between the flange and the end of the first hub-component adjacent the flange.

20. A device according to claim 1, in combination with a skin puncture needle.

21. A device according to claim 1 combination with a supply line arrangement operatively connected with said needle.

22. A device suitable for use in the intermittent or even continuous administration of a therapeutic substance such as insulin, which device comprises:

a cannula of biocompatible plastics material for indwelling in a patient and defining a cannula through-passage;

a hub defining a hub through-passage; and a separator means, the respective cannula and hub through-passages being isolatable from each other by said separator means, said separator means being disposed between the proximal end of the cannula and the proximal end of the hub and the hub being operatively connected with the cannula, the respective said through-passages and said separator means serving, in use, to permit a needle to penetrate the hub and cannula through them and, when necessary, to extend beyond the distal end of the cannula, the through-passage of the hub also serving, in use, to guide an injection needle passed therethrough so that the needle thus guided will pass through the separator means at a position where the needle is aligned with the through-passage of the cannula;

a skin puncture needle;

a supply line arrangement operatively connected with said needle;

the supply line arrangement including mounted on an end portion of a supply line, said needle, being adapted to penetrate the separator means of the device and a pivotal clip engageable with the hub of the device to lock together the device and the supply line.

* * * * *